(12) United States Patent
Pimenta et al.

(10) Patent No.: US 11,607,033 B2
(45) Date of Patent: Mar. 21, 2023

(54) WHITENING SYSTEM

(71) Applicant: Colgate-Palmolive Company, New York, NY (US)

(72) Inventors: Paloma Pimenta, Staten Island, NY (US); Chun Huang, Somerset, NJ (US); Robert Dicosimo, Chadds Ford, PA (US); Mark Payne, Wilmington, DE (US)

(73) Assignee: Colgate-Palmolive Company, New York, NY (US)

( * ) Notice: Subject to any disclaimer, the term of this patent is extended or adjusted under 35 U.S.C. 154(b) by 486 days.

(21) Appl. No.: 16/748,907

(22) Filed: Jan. 22, 2020

(65) Prior Publication Data

US 2020/0229583 A1   Jul. 23, 2020

Related U.S. Application Data (60) Provisional application No. 62/795,167, filed on Jan. 22, 2019.

(51) Int. Cl.
| | |
|---|---|
| *A46B 11/00* | (2006.01) |
| *A46B 9/04* | (2006.01) |
| *A61K 8/22* | (2006.01) |
| *A61K 8/37* | (2006.01) |
| *A61Q 11/00* | (2006.01) |

(52) U.S. Cl.
CPC ............ *A46B 11/0041* (2013.01); *A46B 9/04* (2013.01); *A46B 11/0065* (2013.01); *A61K 8/22* (2013.01); *A61K 8/375* (2013.01); *A61Q 11/00* (2013.01); *A46B 2200/1066* (2013.01)

(58) Field of Classification Search
CPC ... A46B 11/00; A46B 11/0041; A46B 11/003; A46B 11/001; A46B 11/002; A46B 11/0065; A46B 9/04; A46B 2200/1066; A61K 8/22; A61K 8/375; A61K 8/19; A61K 8/37; A61Q 11/00; A61Q 11/02
USPC ...................................... 401/188 R, 270, 282
See application file for complete search history.

(56) References Cited

U.S. PATENT DOCUMENTS

| | | | |
|---|---|---|---|
| 3,901,819 A | 8/1975 | Nakagawa et al. | |
| 7,723,083 B2 | 5/2010 | Dicosimo et al. | |
| 8,293,221 B2 | 10/2012 | Dicosimo et al. | |
| 8,398,325 B2 | 3/2013 | Kennedy | |
| 9,033,602 B2 | 5/2015 | Boyd et al. | |
| 9,180,318 B2 * | 11/2015 | Deng ..................... | A61K 8/365 |
| 9,271,565 B2 | 3/2016 | Mello et al. | |

(Continued)

FOREIGN PATENT DOCUMENTS

| | | |
|---|---|---|
| CN | 106455802 | 2/2017 |
| CN | 101287522 | 10/2018 |

(Continued)

OTHER PUBLICATIONS

International Search Report and Written Opinion in International Application No. PCT/US2020/014502, dated Apr. 21, 2020.

*Primary Examiner* — David J Walczak (57) ABSTRACT

An oral care kit comprising an oral care implement having a first reservoir containing a first oral care agent comprising a first whitening reagent that includes triacetin; and a container having a second reservoir containing a second oral care agent, the second oral care agent comprising a catalytic enzyme and a second whitening reagent that includes peroxide forming compound.

16 Claims, 4 Drawing Sheets

(56) References Cited

U.S. PATENT DOCUMENTS

| | | |
|---|---|---|
| 9,510,668 B2 * | 12/2016 | Patel .................... A46B 11/001 |
| 10,098,824 B2 | 10/2018 | Boyd et al. |
| 10,278,487 B2 | 5/2019 | Wu et al. |
| 10,413,500 B2 | 9/2019 | Gronlund et al. |
| 10,426,719 B2 | 10/2019 | Yuan et al. |
| 10,806,244 B2 | 10/2020 | Davies-Smith et al. |
| 2015/0118167 A1 | 4/2015 | Boyd et al. |
| 2018/0168330 A1 | 6/2018 | Davies-Smith et al. |

FOREIGN PATENT DOCUMENTS

| | | |
|---|---|---|
| RU | 2376917 | 12/2009 |
| RU | 2549315 | 4/2015 |

\* cited by examiner

WHITENING SYSTEM

BACKGROUND

It is frequently desirable to keep formulation components separate prior to use, for example because the components may be too unstable for long-term storage if combined. It is desirable in such cases to be able to mix the formulation components at the point of use in an efficient and simple way.

One example of a formulation where it may be desirable to keep formulation components separate is tooth-whitening formulations comprising reactive ingredients such as peroxides. The difficulty arises in that during use the mixing must be rapid, and diffusion of the bleaching agent to the tooth surface must be efficient. Thus, there is a need for products that permit ingredients to be efficiently and effectively combined at the point of use.

BRIEF SUMMARY

In some embodiments, the present invention is directed to a toothbrush comprising: a body comprising a handle, a head at an end of the handle, and at least one fluid outlet, the head having at least one oral care element extending therefrom; a reservoir in the body containing an oral care agent comprising a whitening reagent, the whitening reagent comprising triacetin; wherein the reservoir is in fluid communication with the fluid outlet.

Other embodiments of the present invention include an oral care kit comprising an oral care implement having a first reservoir containing a first oral care agent comprising a first whitening reagent that includes triacetin; and a container having a second reservoir containing a second oral care agent, the second oral care agent comprising a catalytic enzyme and a second whitening reagent that includes peroxide forming compound.

Other embodiments of the present invention include a method of whitening teeth comprising applying a second oral care agent to a head of an oral care implement, the oral care implement comprising a reservoir containing a first oral care agent comprising triacetin; cleaning an oral cavity with the head of the oral care implement as the first oral care agent is delivered to a fluid outlet on the head from the reservoir, wherein the second oral care agent comprises a peroxide source and a catalytic enzyme.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical,", "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such.

Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used herein, the terms "tooth whitening" and "tooth bleaching" are used interchangeably, to refer to improving the brightness (e.g., whitening) of a tooth or teeth.

As used in herein, "intrinsic stains" in teeth refer to the resulting color from chromogens within the enamel and underlying dentin. The intrinsic color of human teeth tends to become more yellow with aging, due to the thinning of the enamel and darkening of the underlying yellow dentin. Removal of intrinsic stain usually requires the use of peroxides or other oxidizing chemicals, which penetrate the enamel and decolorize the internal chromogens.

In contrast to intrinsic stains, "extrinsic stains" form on the surface of the teeth when exogenous chromogenic materials bind to the enamel, usually within the pellicle naturally coating the teeth. Most people accumulate some degree of unsightly extrinsic stains on their teeth over time. This staining process is promoted by such factors as: (1) the ingestion of tannin-containing foods and beverages such as coffee, tea, or red wine; (2) the use of tobacco products; and/or (3) exposure to certain cationic substances (e.g., tin, iron, and chlorhexidine). These substances tend to adhere to the enamel's hydroxyapatite structure, which leads to tooth discoloration and a concomitant reduction in tooth whiteness. Over a period of years, extrinsic stains may penetrate the enamel layer and result in intrinsic stains.

As used herein, the term "destain" or "destaining" refers to the process of removing a stain from an oral cavity surface. The stain(s) may be intrinsic stains, extrinsic stains, or a combination thereof Unless otherwise specified, all percentages and amounts expressed herein and elsewhere in the specification should be understood to refer to percentages by weight. The amounts given are based on the active weight of the material. According to the present application, the term "about" means+/−5% of the reference value. According to the present application, the term "substantially free" less than about 0.1 wt. % based on the total of the referenced value.

In the following description, each of the exemplary embodiments of the oral care implement of the invention comprises a manually-operated oral care implement, more specifically a manually-operated toothbrush. However, in variations to these embodiments, the oral care implement could instead comprise a powered oral care implement, such as a powered toothbrush, wherein one or more oral care elements provided to the head of the implement are drivable so as to be moved relative to the handle of the implement. In still further embodiments, the oral care implement could instead comprise other forms of oral care implement, such as a soft-tissue cleaner, a tooth polisher, an interdental brush, a tongue scraper, or another implement designed for oral care. It is to be understood that other embodiments may be utilized, and that structural and functional modifications may be made without departing from the scope of the present invention.

Figure 1:
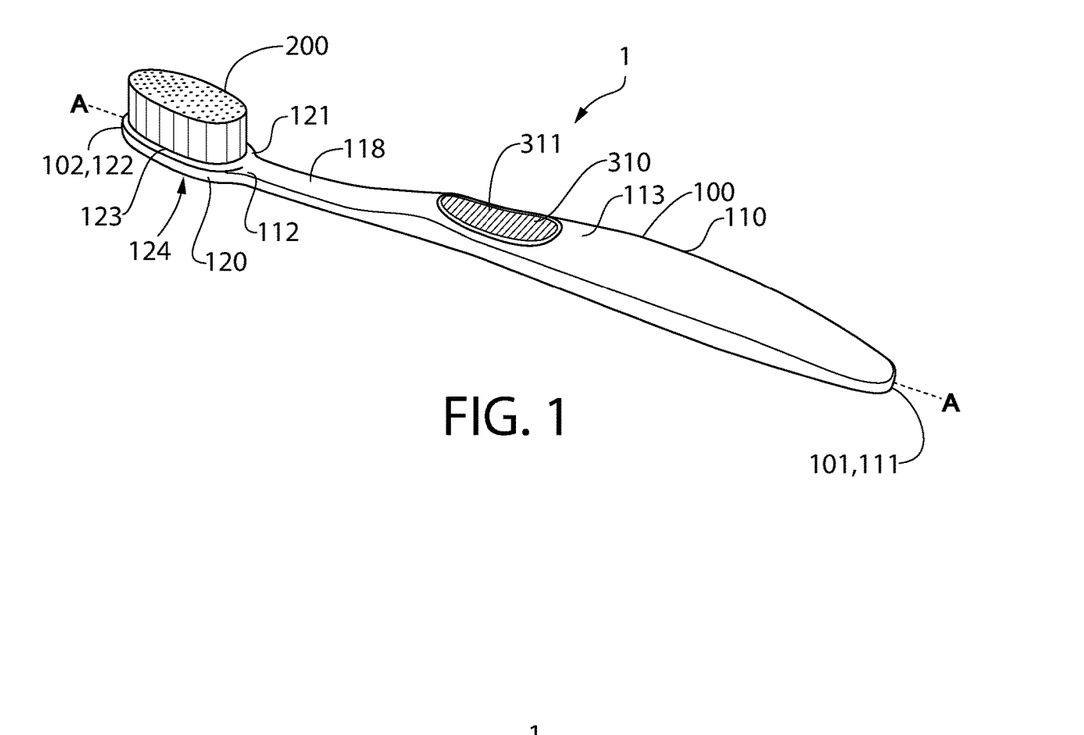
FIG. 1 is perspective view of an oral care implement according to some embodiments of the present invention.
Figure 2:
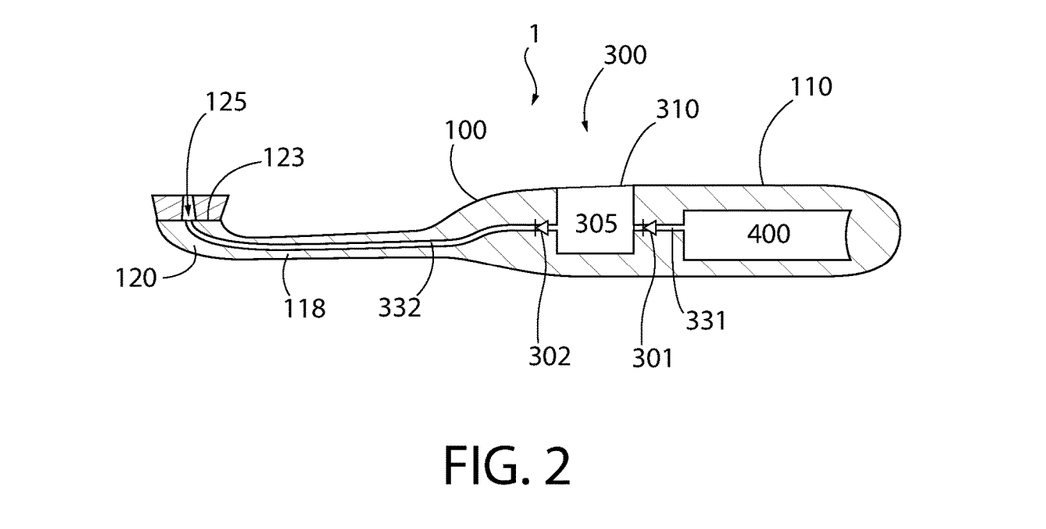
FIG. 2 is a cross-sectional view of the oral care implement of FIG. 1 along line A-A.

Referring now to FIGS. 1 and 2, the present invention includes an oral care implement, in this case a toothbrush, according to an exemplary embodiment of the present invention, generally designated with the reference numeral 1. As viewed from the exterior, the toothbrush 1 generally comprises a body 100, oral care elements 200 and a fluid outlet 125 on a head 120 of the body 100, and a dispensing mechanism 300. In some embodiments the dispensing mechanism 300 may be a pump that is used with a user-operable actuator 310 on a handle 110 of the body 100.

The body 100 of the toothbrush 1 has a proximal end 101 and a distal end 102 and is elongate between the proximal and distal ends 101, 102. The body 100 comprises the handle 110 and the head 120 at a distal end 112 of the handle 110. The head 120 is a distal portion of the body 100 and has a proximal end 121 and a distal end 122, which distal end 122 forms the distal end 102 of the body 100. The head 120 has extending therefrom the oral care elements 200 for cleaning or polishing surfaces in a user's mouth, such as surfaces of their teeth.

The oral care elements 200 extend from a first, front side of the toothbrush 1, more specifically from a first side 123 (also referred to as a "front side") of the head 120 and are for cleaning or polishing surfaces in a user's mouth, such as surfaces of their teeth. As used herein, the term "oral care element" is used in a generic sense to refer to any structure that can be used to clean, massage or polish an oral surface, such as teeth or soft tissue, through relative surface contact. In this embodiment, the oral care elements comprise a plurality of tooth cleaning elements, preferably a plurality of flexible bristles arranged in tufts.

However, in variations to this embodiment, the oral care elements may additionally or alternatively comprise one or more tooth polishing elements, preferably in the form of elastomeric tooth polishing elements, such as elastomeric protrusions, elements, fingers, or prophylactic (prophy) cups. In some embodiments, the oral care elements 200 may comprise at least one of any one or more of the following, without limitation: bristles, rigid bristles, flexible bristles, filament bristles, fiber bristles, nylon bristles, polybutylene terephthalate (PBT) bristles, tapered bristles, spiral bristles, rubber bristles, elastomeric protrusions, elastomeric elements, flexible polymer protrusions, co-extruded filaments, flag bristles, crimped bristles, anti-bacterial bristles and combinations thereof and/or structures containing such materials or combinations.

The oral care elements 200 may be any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The head 120 also comprises the fluid outlet 125 at the first side 123 of the head 120. The fluid outlet 125 will be described in more detail below. In a variation to the illustrated embodiment, a soft tissue cleaner may be provided on a second side of the toothbrush 1, such as a second, rear side of the toothbrush 1 opposite to the front side of the toothbrush 1. Such a soft tissue cleaner may be provided on a second side 124 (also referred to as a "rear side") of the head 120. Although not shown in FIGS. 1-2, the head 120 may comprise the fluid outlet 125 at the second side 124 of the head 120.

The handle 110 is a proximal portion of the body 100 and has the distal end 112 and a proximal end 111, which proximal end 111 forms the proximal end 101 of the body 100. The handle 110 includes a neck portion 118 by which the handle 110 is connected with the head 120. The neck portion 118 is generally of a smaller cross sectional area than the rest of the handle 110. The neck portion 118 includes the distal end 112 of the handle 110, which is that portion of the handle 110 fixed to and closest to the proximal end 121 of the head 120. In the illustrated embodiment, the head 120 is non-detachable from the handle 110. However, in variations to the illustrated embodiment, the head 120 may be detachable from the handle 110, such as for replacement of the head 110 when the oral care elements 200 become worn.

The handle 110 provides a user with a mechanism by which he/she can readily grip and manipulate the toothbrush 1, includes ergonomic features which provide a high degree of control for the user while maintaining comfort, and may be formed of many different shapes and with a variety of constructions. Although the handle 110 is a non-linear structure in the illustrated embodiment, the invention is not so limited, and in certain embodiments the toothbrush 1 may have a simple linear handle 110.

Figure 3:
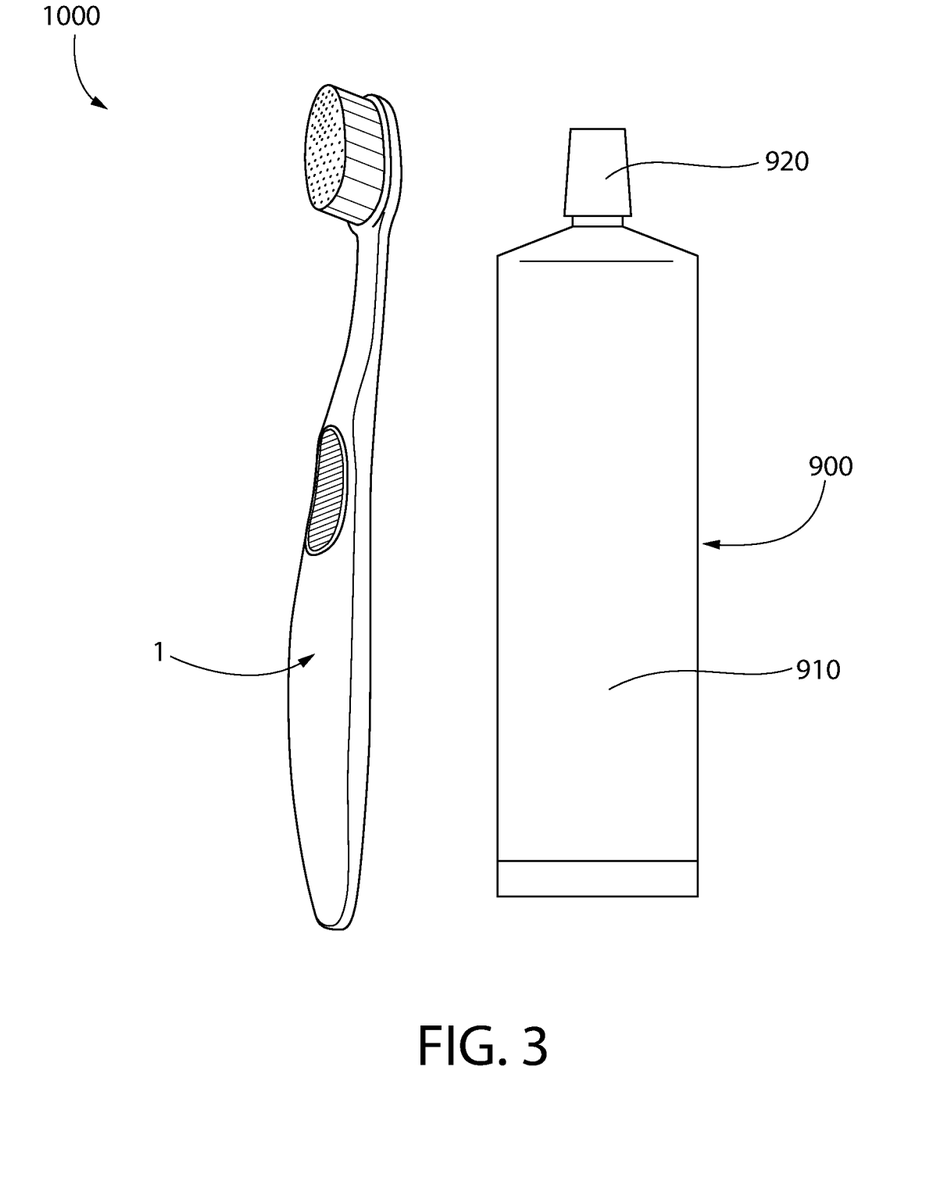
FIG. 3 is a kit comprising the oral care implement and a container.

As best shown in FIGS. 2 and 3, the toothbrush 1 comprises a reservoir 400 in the handle 110 of the body 100. The reservoir 400 of the toothbrush may be referred to as the "first reservoir" 400. In the illustrated embodiment, the reservoir 400 is comprised in a vessel formed from a plastic, such as a thermoplastic polymer, e.g. polyethylene terephthalate (PET) or polypropylene (PP), is housed inside the body 100 of the toothbrush 1 and is not visible from the exterior of the toothbrush 1. However, in variations to the illustrated embodiment, the reservoir 400 is made of transparent or translucent material and one or more windows are provided in the body 100, so that the reservoir 400 and its contents are visible from the exterior of the toothbrush 1. In further embodiments, the body 100 comprises the reservoir 400 and the reservoir 400 forms at least part of the handle 110. In some embodiments, the reservoir 400 is detachably connected to the body 100 and may be replaceable or disposable.

According to the present invention, the first reservoir 400 may contain a first oral care agent. The first oral care agent may comprise a first whitening reagent. In a non-limiting example, the first whitening reagent may comprise one or more esters having the structure"

Wherein:

X is an ester group of the formula $R_6C(O)O$;

$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety or a cyclic five-membered heteroaromatic or six-membered cyclic aromatic or heteroaromatic moiety optionally substituted with a hydroxyl group; wherein each carbon atom in $R_5$ individually comprises no more than one hydroxyl group or no more than one ester group, and wherein $R_5$ optionally comprises one or more ether linkages;

m is an integer ranging from 1 to the number of carbon atoms in $R_5$, said one or more esters having solubility in water of at least 5 ppm at 25° C.

The first whitening reagent may be an acetin compound—including a monoacetin, a diacetin, and/or a triacetin. As used herein, the term "monoacetin" is synonymous with glycerol monoacetate, glycerin monoacetate, and glyceryl monoacetate. As used herein, the term "diacetin" is synonymous with glycerol diacetate; glycerin diacetate, glyceryl diacetate, and all other synonyms of CAS Registry Number 25395-31-7. As used herein, the term "triacetin" is synonymous with glycerin triacetate; glycerol triacetate; glyceryl triacetate, 1,2,3-triacetoxypropane; 1,2,3-propanetriol triacetate and all other synonyms of CAS Registry Number 102-76-1.

In some embodiments, the first whitening reagent may comprise triacetin. In some embodiments, the first whitening reagent may consist essentially of triacetin. The first whitening reagent may be substantially free of a peroxide source, such as hydrogen peroxide.

The first whitening reagent may be delivered in an amount ranging from about 10 ppm to about 1000 ppm—including all amounts and sub-ranges-there-between.

The first oral care agent may further comprise flavors or flavor ingredients, and breath freshening ingredients, enamel strengthening or repair agents; tooth erosion preventing agents; tooth anti-sensitivity ingredients; gum health actives; nutritional ingredients; tartar control or anti-stain ingredients; enzymes; sensate ingredients; caries or plaque disclosing agents. The first oral care agent may further comprise an orally-acceptable carrier.

The orally acceptable carrier may be delivered in the first whitening agent in an amount ranging from about 10 ppm to about 1000 ppm—including all amounts and sub-ranges-there-between.

As shown in FIG. 2, in some embodiments the toothbrush 1 may comprise the pump 300 in the body 100, whereby the pump 300 is for pumping the first oral care agent from the first reservoir 400 in the handle 110 to the fluid outlet 125 of the head 120. The pump 300 comprises a first check valve 301, a second check valve 302 downstream from the first check valve 301, and a chamber 305 of variable volume between the first and second check valves 301, 302. That is, the first check valve 301 is downstream of the reservoir 400 and upstream of the chamber 305, the chamber 305 is downstream of the first check valve 301 and upstream of the second check valve 302, and the second check valve 302 is downstream of the chamber 305.

The first reservoir 400 may be fluidly connected to the first check valve 301 by a first passageway 331, and the second check valve 302 may be fluidly connected to the fluid outlet 125 by a second passageway 332. In the illustrated embodiment, the first passageway 331 may be formed by material of the body 100. In variations to the illustrated embodiment, some or a majority of the first passageway 331 may be formed by a separate tube that extends through the body 100. Also, in the illustrated embodiment, a majority of the second passageway 332 is defined by a, preferably flexible, tube that extends through the neck portion 118 of the body 100. In variations to the illustrated embodiment, some or a majority of the second passageway 332 may be defined by material of the body 100.

The fluid outlet 125 may be of any form known in the art. The fluid outlet 125 may permanently permit fluid communication from the exterior of the toothbrush 1 to the second passageway 332, or the fluid outlet 125 may comprise a valve, such as a check valve, that permits fluid flow from the second passageway 332 to the exterior of the toothbrush 1 and restricts or prevents fluid flow from the exterior of the toothbrush 1 to the second passageway 332.

The first oral care agent may be delivered to the first side 123 of the head 120 via the fluid outlet 125, whereby the first oral care agent reaches the oral care elements 200 (such as bristles) extending from the first side 123 of the head 120. In other embodiments, the first oral care agent may be delivered to the second side 124 of the head 120 via the fluid outlet 125, whereby the first oral care agent reaches the oral care elements 200 (such as soft-tissue cleaner) extending from the second side 124 of the head 120.

Optionally, the fluid outlet 125 includes a spray or atomizer nozzle for causing the oral care fluid to be emitted as one of a spray, a mist, and a stream. Such a nozzle optionally causes the oral care fluid to be emitted in the form of droplets having an average diameter of less than 500 microns, or less than 400 microns, or less than 300 microns, or less than 200 microns, or less than 150 microns.

Referring now to FIG. 3, the present invention may further comprise a kit 1000 that includes the oral care implement 1 as well as a container 900. The container 900 may be physically separate from the oral care implement 1. The container 900 may be a toothpaste container comprising a second reservoir 910 and a removable cap 920 for containing the second reservoir 910.

The second container 910 may contains a second oral agent. The second oral agent may be a dentifrice composition. The second oral agent may comprise a second whitening reagent.

In a non-limiting embodiment, the second whitening reagent may comprise a peroxygen source. The term "peroxygen source" and "source of peroxygen" refer to compounds capable of providing hydrogen peroxide at a concentration of about 1 mM or more when in an aqueous solution including, but not limited to, hydrogen peroxide, hydrogen peroxide adducts (e.g., urea-hydrogen peroxide adduct (carbamide peroxide)), perborates, and percarbonates.

The second whitening reagent may be present in the second whitening agent in an amount ranging from about 10 ppm to about 1000 ppm—including all amounts and sub-ranges-there-between.

The second oral agent may further comprise an enzyme catalyst. The term "enzyme catalyst" or "catalytic enzyme" refers to a catalyst comprising an enzyme having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (such as by pegylation or by reaction with cross-linking reagents). The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997.

The enzyme catalyst may be present in the second whitening agent in an amount ranging from about 10 ppm to about 1000 ppm—including all amounts and sub-ranges-there-between.

Non-limiting examples of the catalytic enzyme include acetyl xylan esterases, which refers to an enzyme (E.C. 3.1.1.72; AXEs) that catalyzes the deacetylation of acetylated xylans and other acetylated saccharides.

Other non-limiting examples include cephalosporin C deacetylase and cephalosporin C acetyl hydrolase, which refer to an enzyme (E.C. 3.1.1.41) that catalyzes the deacetylation of cephalosporins such as cephalosporin C and 7-aminocephalosporanic acid (Mitsushima et al., (1995) *Appl. Env. Microbiol.* 61(6):2224-2229). The amino acid sequences of several cephalosporin C deacetylases having significant perhydrolytic activity are provided herein.

Another non-limiting example of the catalytic enzyme includes *Bacillus subtilis*, which refers to a bacterial cell deposited to the American Type Culture Collection (ATCC) having international depository accession number ATCC® 31954™. Another non-limiting example is *Thermotoga maritima*, refers to a bacterial cell reported to have acetyl xylan esterase activity—see U.S. Patent Application Publication No. 2008-0176299.

The term "amino acid" refers to the basic chemical structural unit of a protein or polypeptide. The following abbreviations are used herein to identify specific amino acids: alanine, arginine, asparagine, aspartic acid, cysteine, glutamine, glutamic acid, glycine, histidine, isoleucine, leucine, lysine, methionine, pheylalanine, proline, serine, threonine, typtophan, tyrosine, and valine.

Operation of the illustrated toothbrush 1 will now be described. A user may apply the second oral care agent to the oral care elements 200 and then uses the second oral care agent and the oral care elements 200 to brush their teeth. In order to benefit from the effects of the first oral care agent in the first reservoir 400, before, during or after brushing their teeth, while holding the head 120 in their oral cavity, the user applies a force onto the thumb grip surface 311 in a direction substantially towards the longitudinal axis A-A of the toothbrush 1.

Application of the force causes the diaphragm 310 to move inwards toward the body 110, thereby to reduce the volume of the chamber 305. The reduction in volume of the chamber 305 increases pressure of fluid in the chamber 305. As will be appreciated by the skilled person, the increased pressure of the fluid in the chamber 305 causes the fluid in the chamber 305 to apply a force to the second check valve 302 to overcome the resilience of the second check valve 302. The second check valve 302 thus opens, and the fluid in the chamber 305 passes through the second check valve 302 into the second passageway 332. Meanwhile, the first check valve 301 remains closed, because the pressure in the chamber 305 is greater than that in the first passageway 331. The second check valve 302 remains open until the pressure in the chamber 305 and the pressure in the second passageway 332 are substantially equal, at which point the second check valve 302 closes.

When the user subsequently reduces or removes the force F, the resilience of the diaphragm 310 causes the diaphragm 310 to move outward, thereby to increase the volume of the chamber 305 and correspondingly reduce the pressure of fluid in the chamber 305. Initially, during this movement of the diaphragm 310 away from the base, both the first and second check valves 301, 302 are closed. However, once the pressure of fluid in the chamber 305 drops to below the pressure of fluid in the first passageway 331, the higher pressure of the fluid in the first passageway 331 causes the fluid in the first passageway 331 to apply a force to the first check valve 301 to overcome the resilience of the first check valve 301. The first check valve 301 thus opens, and the fluid in the first passageway 331, comprising oral care fluid from the first reservoir 400, passes through the first check valve 301 into the chamber 305. Meanwhile, the second check valve 302 remains closed, because the pressure in the second passageway 332 is greater than that in the chamber 305. Once the pressure in the chamber 305 and the pressure in the first passageway 331 are substantially equal, the resilience of the first check valve 301 causes the first check valve 301 to close.

As will be understood by the skilled person, by reapplying the force F, the oral care fluid now in the chamber 305 passes through the second check valve 302. Repeated application and removal of the force causes a net movement of the first oral care agent from the first reservoir 400 to the fluid outlet 125 and the exterior of the toothbrush 1.

Once the first oral care agent and the second oral care agent combine and mix together in the presence of salvia, the first and second oral care reagents will react in the presence of the catalytic enzyme to form a peracid. As used herein, the term "peracid" is synonymous with peroxyacid, peroxycarboxylic acid, peroxy acid, percarboxylic acid and peroxoic acid. As used herein, the term "peracetic acid" is abbreviated as "PAA" and is synonymous with peroxyacetic acid, ethaneperoxoic acid and all other synonyms of CAS Registry Number 79-21-0.

The presence of the peracid during brushing provides a surprising increasing in whitening efficacy of the second oral care agent—thereby improving the removal of both intrinsic and extrinsic stains in and on a user's tooth.

In one embodiment, the peroxygen source may be present in an amount such that hydrogen peroxide concentration in the aqueous reaction formulation is at least 0.5 mM. In one embodiment, the hydrogen peroxide concentration in the aqueous reaction formulation is at least 1 mM. In another embodiment, the hydrogen peroxide concentration in the aqueous reaction formulation is at least 10 mM. In another embodiment, the hydrogen peroxide concentration in the aqueous reaction formulation is at least 100 mM. In another embodiment, the hydrogen peroxide concentration in the aqueous reaction formulation is at least 200 mM. In another embodiment, the hydrogen peroxide concentration in the aqueous reaction formulation is 500 mM or more. In yet another embodiment, the hydrogen peroxide concentration in the aqueous reaction formulation is 1000 mM or more.

The amount of the first oral care agent delivered to the fluid outlet 125 may be an effective amount of catalytic enzyme. As used herein, "effective amount of catalytic enzyme" refers to the quantity of enzyme necessary to achieve the enzymatic activity required for the first and second oral care reagents to react, thereby generating a peracid. Such effective amounts are readily ascertained by one of ordinary skill in the art and are based on many factors, such as the particular enzyme variant used.

Figure 4:
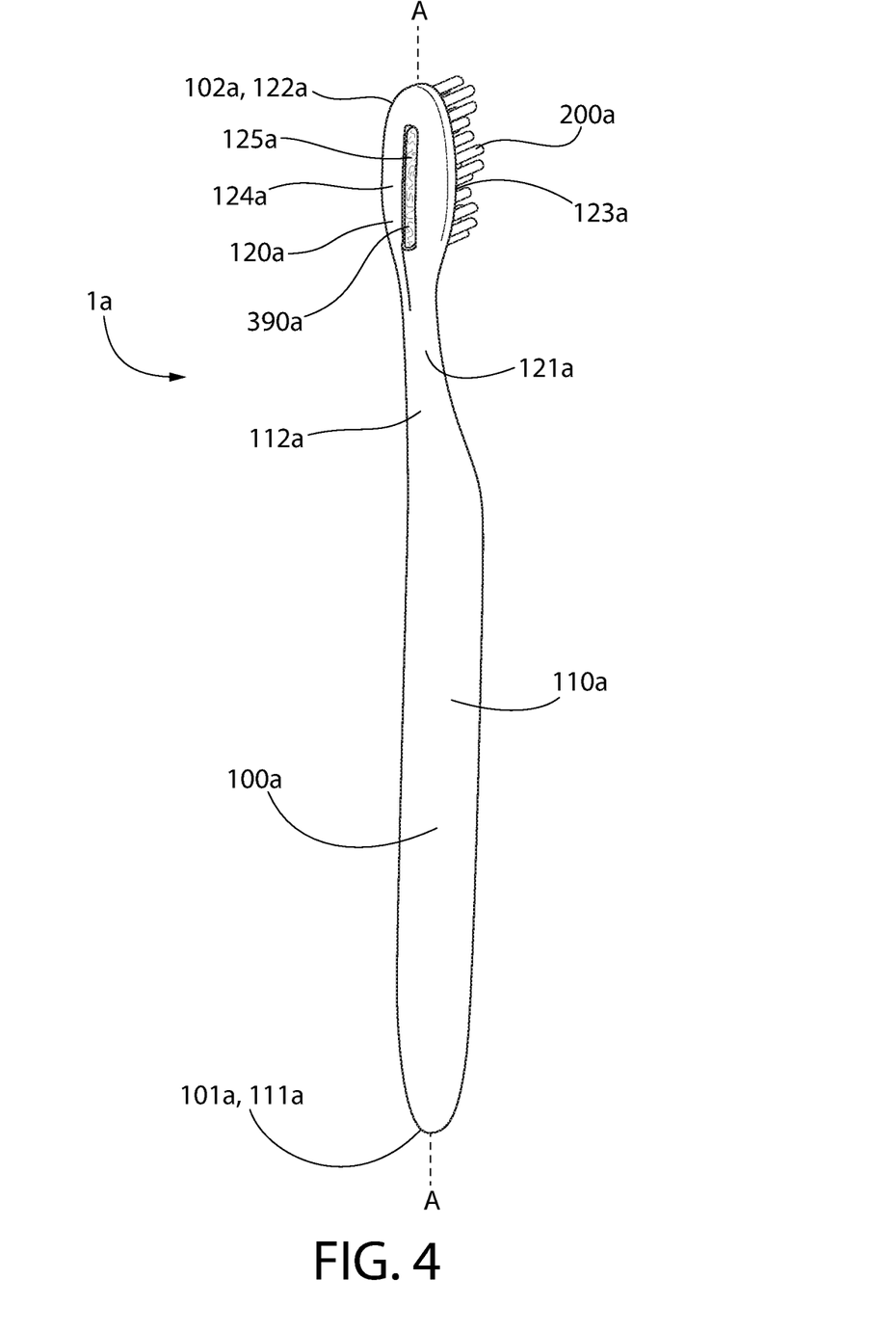
FIG. 4 is a perspective view of an oral care implement according to another embodiment of the present invention.
Figure 5:
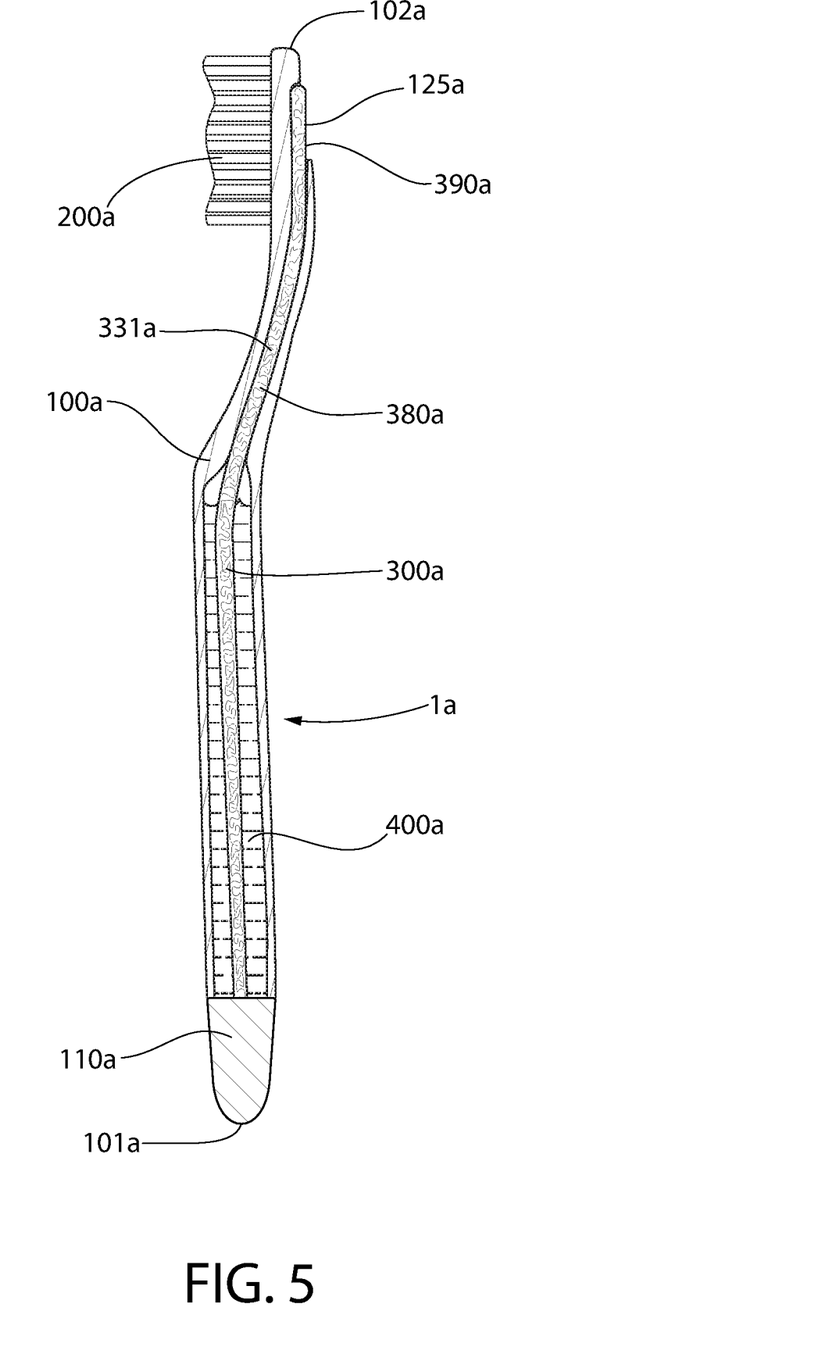
FIG. 5 is a cross-sectional view of the oral care implement of FIG. 4 along line A-A.

Referring now to FIGS. 4 and 5, an oral care implement 1a is illustrated in accordance with another embodiment of the present invention. The oral care implement 1a is similar to the oral care implement 1 except as described herein below. The description of the oral care implement 1 above generally applies to the oral care implement 1a described below except with regard to the differences specifically noted below. A similar numbering scheme will be used for the oral care implement 1a as with the oral care implement 1 except that an "a" suffix will be used.

According to this embodiment, the dispensing mechanism 300a may comprise a fluid delivery member 380a and an applicator 390a. The fluid delivery member 380a may be in direct fluid communication with the first reservoir 400a. The applicator 390a may be in direct fluid communication with the fluid outlet 125a. The delivery member 380a may extend from the first reservoir 400a to the applicator 390a at the fluid outlet 125a through a passageway 331a.

The fluid delivery member 380a may be an elongated rod constructed of a capillary material. Non-limiting examples of capillary material include one or more of a porous material, a fibrous material, woven material, non-woven material, a cellular material, a non-cellular materials, and a material comprising one or more capillary channels.

The fluid delivery member 380a and the applicator 390a may be integral to one another and of a unitary construct. However, in other embodiments, the fluid delivery member 380a and the applicator 390a may be separate and distinct components and/or structures that are fluidly and/or structurally coupled together when the toothbrush 1a is assembled.

The applicator 390a is at least partially disposed within the channel 331a and is in fluid communication with the first oral care agent within the first reservoir 400a. In the exemplified embodiment, the fluid communication between the applicator 390a and the first oral care agent within the first reservoir 400a can be considered "indirect fluid communication" due to the existence of a fluid delivery member 380a. In certain non-illustrated embodiments, the applicator 390a may be in direct fluid communication with the first oral care agent within the first reservoir 400a due to the applicator 390a being positioned closely (proximate) to the first reservoir 400a or the applicator 390a being appropriately sized.

The fluid delivery member 380a extends between the first reservoir 400a and the applicator 390a to effectuate the fluid communication between the applicator 390a and the first oral care agent within the reservoir 400a. Both the fluid delivery member 380a and the applicator 390a may be formed of the capillary material so that the first oral care agent is delivered from the first reservoir 400a to the applicator 390a via capillary action. In one embodiment, the delivery of the first oral care agent from the first reservoir 400a to the applicator 390a is effectuated solely by capillary action.

In a certain embodiment, the first oral care agent may be continuously delivered to the applicator 390a (either directly or indirectly) from the first reservoir 400a by capillary action. It should be understood that in certain embodiments, the first oral care agent may be delivered from the first reservoir 400a to the applicator 390a solely by capillary action.

According to these embodiments, the first oral care agent may be delivered to the applicator 390a positioned on the second side 124a of the head 120a via the fluid outlet 125a by capillary action. The first oral care agent may reach any oral care element positioned on the second side 124a of the head 120a (such as a soft tissue cleaner). Although not pictured, the present invention includes other embodiments, where the first oral care agent may be delivered to the first side 123a of the head 120a via the fluid outlet 125a by capillary action. The first oral care agent may reach any the oral care element 200a positioned on the first side 124a of the head 120a (such as bristles).

The invention will be described in greater detail by way of specific examples. The following examples are offered for illustrative purposes and are not intended to limit the invention in any manner.

EXAMPLES

Experiment 1

A first experiment was performed to measure the amount of acetic peracid ("PAA") formed in a brushing slurry based on the combination of the first oral care agent and the second oral care agent. The amount of acetic peracid is indicative of whitening efficacy of the oral care system.

The experiment tested a first oral care agent with a variety of second oral care agents. The first oral care agent comprises triacetin. The second oral care agent is a toothpaste having varying amounts of enzyme and hydrogen peroxide. The formulation of the first and second oral care agents are forth below in Table 1.

TABLE 1

|  | First Oral Care Agent | Second Oral Care Agent | |
| --- | --- | --- | --- |
| Control | — | Enzyme 0 wt. % | Hydrogen Peroxide 1.0 wt. % |
| Ex. 1 | Triacetin | Enzyme 0 wt. % | Hydrogen Peroxide 0.1 wt. % |
| Ex. 2 | Triacetin | Enzyme 0 wt. % | Hydrogen Peroxide 1.0 wt. % |
| Ex. 3 | Triacetin (150 mg) | Enzyme 0.1 wt. % | Hydrogen Peroxide 0.1 wt. % |
| Ex. 4 | Triacetin (300 mg) | Enzyme 0.1 wt. % | Hydrogen Peroxide 0.1 wt. % |

TABLE 1-continued

|  | First Oral Care Agent | Second Oral Care Agent | |
|---|---|---|---|
| Ex. 5 | Triacetin (450 mg) | Enzyme 0.1 wt. % | Hydrogen Peroxide 0.1 wt. % |
| Ex. 6 | Triacetin (50 mg) | Enzyme 0.1 wt. % | Hydrogen Peroxide 1.0 wt. % |
| Ex. 7 | Triacetin (100 mg) | Enzyme 0.1 wt. % | Hydrogen Peroxide 1.0 wt. % |
| Ex. 8 | Triacetin (150 mg) | Enzyme 0.1 wt. % | Hydrogen Peroxide 1.0 wt. % |
| Ex. 9 | — | Enzyme 0.1 wt. % | Hydrogen Peroxide 1.0 wt. % |

Each formulation of Ex. 1-8 were blended together with the addition of 10 g of water and mixed at 1500 rpm for 2 minutes. After mixing, phosphoric acid was added to each formulation and vortexed for 30 seconds to terminate the enzyme reaction. Additional MTS and TPP reagent were added to the mixture, and subsequently vortexed again and allowed to react in in the dark for 30 minutes. After this period, each mixture was evaluated for the amounts of PPA (measured in ppm). The results are set forth below in Table 2.

TABLE 2

|  | Ex. 3 | Ex. 4 | Ex. 5 | Ex. 6 | Ex. 7 | Ex. 8 |
|---|---|---|---|---|---|---|
| PPA Concentration (ppm) | 275 | 417 | 562 | 399 | 663 | 1062 |

As demonstrated by Table 2, for toothpaste (i.e., the second oral care agent) having same amount of hydrogen peroxide, the more triacetin added results in greater amount of PAA being generated. For example, the a formulation having 0.1 wt. % of hydrogen peroxide/0.1 wt. % of enzyme and 150 mg triacetin will generate ~275 ppm PAA, while the PAA concentration will rise to 417 ppm and 562 ppm respectively when 300 mg and 450 mg triacetin is used. Surprisingly, similar levels of PAA can be generated using lower amounts of triacetin when the amount of hydrogen peroxide is used. For example, compare Examples 6 and 7 versus Example 3.

Experiment 2

A second experiment was performed to measure the whitening efficacy of the whitening system of the present invention. The experiment tested the Control Formulation against Examples 2 and 9. Identical amounts of each formulation were then brushed onto artificially stained bovine central incisors with the addition of 10 g of artificial saliva. The change in color (i.e., whitening effect) for each formulation was measured over the course of four separate brushing treatments. The change in color evaluations were performed by measured initial color of the stained bovine incisors and the change in color over the course of 4 separate brushing treatments. The initial and subsequent color measurement and the subsequent color measurements were obtained using stand L* a* b* color measurements, whereby the change in color ($\Delta W$) using the following calculation:

$$\Delta W = [(L_2 - L_1)^2 + (a_2 - a_1)^2 + (b_2 - b_1)^2]^{1/2}$$

The change in color for each treatment is set forth below in Table 2.

TABLE 3

|  | Control | Ex. 9 | Ex. 2 |
|---|---|---|---|
| Treatment 1 | 1.5 | 1.4 | 2.3 |
| Treatment 2 | 2.6 | 2.7 | 3.9 |
| Treatment 3 | 3.1 | 3.3 | 4.6 |
| Treatment 4 | 3.3 | 3.5 | 5.2 |

As demonstrated by Table 3, the combination of the first oral agent comprising triacetin with the second oral agent comprising hydrogen peroxide and enzyme gave a significantly better whitening efficacy compared to the teeth treated with only the hydrogen peroxide and enzyme toothpaste or control formulation having no enzyme at all. The improved whitening efficacy is attributed to the in-situ generation of PAA.

What is claimed is:

1. An oral care implement comprising:
   a body comprising a handle, a head at an end of the handle, and at least one fluid outlet, the head having at least one oral care element extending therefrom;
   a reservoir in the body containing an oral care agent comprising a whitening reagent, the whitening reagent consisting of triacetin;
   wherein the reservoir is in fluid communication with the fluid outlet.

2. The oral care implement according to claim 1, wherein the oral care agent is substantially free of a peroxide source.

3. The oral care implement according to claim 1, wherein the whitening reagent is present in an amount ranging from 10 ppm to about 1000 ppm.

4. The oral care implement according to claim 1, wherein the oral care agent further comprises an orally acceptable carrier in an amount ranging from about 10 ppm to about 1000 ppm.

5. The oral care implement according to claim 1, wherein the fluid outlet is located on the head.

6. An oral care kit comprising
   an oral care implement having a first reservoir containing a first oral care agent comprising a first whitening reagent that includes triacetin; and
   a container having a second reservoir containing a second oral care agent, the second oral care agent comprising a catalytic enzyme and a second whitening reagent that includes peroxide forming compound.

7. The oral care kit according to claim 6, wherein the first whitening reagent consists of triacetin.

8. The oral care kit according to claim 6, wherein the first oral care agent is substantially free of a peroxide source.

9. The oral care kit according to claim 6, wherein the first whitening reagent is present in an amount ranging from about 10 ppm to about 1000 ppm based on the total weight of the first oral care agent.

10. The oral care kit according to claim 6, wherein the second whitening reagent comprises hydrogen peroxide.

11. The oral care kit according to claim 6, wherein the second whitening reagent is present in an amount ranging from about 10 ppm to about 1000 ppm.

12. The oral care kit according to claim 6, wherein the catalytic enzyme is present in an amount ranging from about 0.01 wt. % to about 1 wt. % based on the total weight of the second oral care agent.

13. The oral care kit according to claim 6, wherein the oral care implement is a toothbrush, wherein the container is a toothpaste container and the second oral care agent is dentifrice.

14. A method of whitening teeth comprising
applying a second oral care agent to a head of an oral care implement, the oral care implement comprising a reservoir containing a first oral care agent comprising triacetin;
cleaning an oral cavity with the head of the oral care implement as the first oral care agent is delivered to a fluid outlet on the head from the reservoir,
wherein the second oral care agent comprises a peroxide source and a catalytic enzyme.

15. The method according to claim 14, wherein the triacetin is present in an amount ranging from about 10 ppm to about 1000 ppm upon delivery.

16. The method according to claim 14, wherein the catalytic enzyme is present in an amount ranging from about 0.001 wt. % to about 1 wt. % based on the total weight of the second oral care agent.

* * * * *